US010201566B2

(12) United States Patent
Fuchs

(10) Patent No.: US 10,201,566 B2
(45) Date of Patent: Feb. 12, 2019

(54) PHARMACEUTICAL PREPARATION CONTAINING SELENITE OR SELENITE-CONTAINING COMPOUNDS FOR TREATING CERVICAL DYSPLASIA OR CARCINOMAS

(75) Inventor: Norbert Fuchs, Mariapfarr (AT)

(73) Assignee: SELO MEDICAL GMBH, Unternberg (AT)

( * ) Notice: Subject to any disclaimer, the term of this patent is extended or adjusted under 35 U.S.C. 154(b) by 0 days.

(21) Appl. No.: 14/000,133

(22) PCT Filed: Feb. 16, 2012

(86) PCT No.: PCT/AT2012/000032
§ 371 (c)(1),
(2), (4) Date: Aug. 16, 2013

(87) PCT Pub. No.: WO2012/109685
PCT Pub. Date: Aug. 23, 2012

(65) Prior Publication Data
US 2013/0323328 A1 Dec. 5, 2013

(30) Foreign Application Priority Data
Feb. 16, 2011 (AT) .................. A 201/2011

(51) Int. Cl.
A61K 33/04 (2006.01)
A61K 9/00 (2006.01)
A61K 45/06 (2006.01)
A61K 9/06 (2006.01)
A61K 47/38 (2006.01)

(52) U.S. Cl.
CPC ............ A61K 33/04 (2013.01); A61K 9/0034 (2013.01); A61K 9/0036 (2013.01); A61K 9/06 (2013.01); A61K 45/06 (2013.01); A61K 47/38 (2013.01)

(58) Field of Classification Search
CPC ............................. A61K 33/04; A61K 9/0036
See application file for complete search history.

(56) References Cited

U.S. PATENT DOCUMENTS

| | | | |
|---|---|---|---|
| 4,512,977 A | 4/1985 | Lundy | |
| 4,668,515 A | 5/1987 | Bankit et al. | |
| 4,681,753 A | 7/1987 | Revici | |
| 4,762,726 A | 8/1988 | Soucie et al. | |
| 5,153,230 A | 10/1992 | Jeffery | |
| 5,182,104 A | 1/1993 | Marcus et al. | |
| 5,425,944 A | 6/1995 | Harich | |
| 5,470,880 A | 11/1995 | Yu et al. | |
| 5,512,200 A | 4/1996 | Garcia | |
| 5,536,497 A | 7/1996 | Evans et al. | |
| 6,069,152 A | 5/2000 | Schaus et al. | |
| 6,114,348 A | 9/2000 | Weber et al. | |
| 6,120,758 A | 9/2000 | Siddiqui et al. | |
| 6,133,237 A | 10/2000 | Noll et al. | |
| 6,277,835 B1 | 8/2001 | Brown | |
| 6,391,323 B1 | 5/2002 | Carnevali | |
| 2003/0180387 A1 | 9/2003 | Kossler et al. | |
| 2005/0048134 A1* | 3/2005 | Kuklinski | A61K 33/04 424/702 |

FOREIGN PATENT DOCUMENTS

| | | |
|---|---|---|
| DE | 3408362 | 9/1984 |
| DE | 4320694 | 1/1995 |
| DE | 4335441 | 4/1995 |
| DE | 4413839 | 10/1995 |
| EP | 0000670 | 2/1979 |
| EP | 0750911 | 1/1997 |
| EP | 0913155 | 5/1999 |
| FR | 2779720 | 12/1999 |
| GB | 2323030 | 9/1998 |
| WO | WO2000/012101 | 3/2000 |
| WO | WO2000/028977 | 5/2000 |
| WO | WO 2001/093910 | 12/2001 |
| WO | WO2001/093910 | 12/2001 |
| WO | WO2002/072112 | 9/2002 |
| WO | WO 2003/047604 | 6/2003 |

OTHER PUBLICATIONS

Rudolf, E.; Rudolf, K.; Cervinka, M. "Selenium activates p53 and p38 pathways and induces caspase-independent cell death in cervical cancer cells" Cell Biol Toxicol 2008, 24, 123-141.*
Medline "http://www.nlm.nih.gov/medlineplus/ency/article/001491. htm" as published Dec. 31, 2009.*
Schiffman, M.; Castle, P.E.; Jeronimo, J.; Rodriquez, A.C.; Wacholder, S. "Human papillomavirus and cervical cancer" The Lancet 2007, 370, 890-907.*
Crowley, M.M. "Solutions, Emulsions, Suspensions, and Extracts" Chapter 39. Remington: The Science and Practice of Pharmacy, 21st Edition, 2005, 745-775.*
Hong et al. "Detection of level of slenium in cervical tissues of patients with human papillomavirus infection" Zhongguo Redai Yixue (2008), 8(8), 1315-1316 (English abstract).*
"Supplementation" (http://www.thefreedictionary.com/supplementation) accessed Jan. 31, 2017, p. 1.*
Crowley, M.M. "Solutions, Emulsions, Suspensions, and Extracts" Chapter 39. Remington: The Science and Practice of Pharmacy, 21st Edition, 2005, 745-775. (Year: 2005).*

(Continued)

Primary Examiner — Andrew S Rosenthal
(74) Attorney, Agent, or Firm — Norton Rose Fulbright US LLP

(57) ABSTRACT

The invention relates to compositions containing selenite-containing compounds and pharmaceutically acceptable acids, selected from citric acid, acetic acid, malic acid, carbonic acid, sulphuric acid, nitric acid, hydrochloric acid, fruit acids or mixtures thereof, for use for treating cervical inflammations, dysplasia and/or carcinomas. The invention further relates to methods of using such compositions.

21 Claims, No Drawings

(56) References Cited

OTHER PUBLICATIONS

Hong et al. "Detection of level of slenium in cervical tissues of patients with human papillomavirus infection" Zhongguo Redai Yixue (2008), 8(8), 1315-1316 (English abstract) (Year: 2008).*
Kim, S.Y. et al. "Changes in Lipid Peroxidation and Antioxidant Trace Elements in Serum of Women With Cervical Intraepithelial Neoplasia and Invasive Cancer" Nutrition and Cancer vol. 47, Issue 2, 2003, pp. 126-130 (Year: 2003).*
Fu et al., "Proteomic study on sodium selenite-induced apoptosis of human cervical cancer HeLa cells", *Journal of Trace Elements in Medicine and Biology*, 25(3):130-137, 2011.
International Preliminary Report on Patentability issued in PCT Application No. PCT/AT2012/00032, dated Aug. 21, 2013.
International Search Report issued in PCT Application No. PCT/AT2012/00032, dated Apr. 4, 2012.
Office Communication issued in Austrian Patent Application No. A 201/2011, dated Sep. 6, 2011.
Rudolf et al., "Selenium activates p53 and p38 pathways and induces caspase-independent cell death in cervical cancer cells", *Cell Biology and Toxicology*, 24(2):123-141, 2007.
"Bromelains," Reynolds Jef (Editor). Martindale: The Extra Pharmacopeia (Twenty-Eight Edition). The Pharmaceutical Press, London, pp. 646, 1982.
"Hydroxy Acid," Stedman's Medical Dictionary (Twenty-Second Edition). Williams and Wilkins Company, pp. 595, 1972.
"Melanoma," The Merck Manual-Second Home Edition [Online] 1995-2000.
"Preventive" and "Prophylactic," Stedman's Medical Dictionary (Twenty-Second Edition). Williams and Wilkins Company, pp. 1017, 1025, 1972.
"Vitamin C," Stedman's Medical Dictionary (Twenty Fifth Edition). Williams and Wilkins, pp. 1725-1726, 1990.
Carey, "Carbonic Acid," Organic Chemistry (Fourth Edition). McGraw Hill, pp. 749, 2000.
Eisenberg et al., ""Interactions of Selenium and Fluoride on Growth, Glycolysis and Survival of *Streptococcus mutans* GS-5"", *Caries Research*, 1990, 24, 306-311.
Emmert, "Treatment of Common Cutaneous Herpes Simplex Virus Infections," *American Family Physician*, 61:1697-1706, 1708, 2000.
English et al., "Dermatoses of the glans penis and prepuce" *Journal of the American Academy of Dermatology*, 37(1): 1-24, 1997 (Abstract).
Ganther, "Metabolism of hydrogen selenide and methylated selenides," Advances in Nutrional Research, Draper HH, editor, New York-Plenum Press, 2:107-128, 1979.
Gonzalez, "Ascorbic Acid and Selenium Interaction: Its Relevance in Carcinogenesis", Journal of Orthomolecular Medicine, vol. 5, No. 2, 1990, pp. 67-69.
Haas et al., "The Pathogenesis of Hemorrhoids" *Dis Colon Rectum*, 27: 442-50. 1984.

Ismail et al., "Prevention of periodontal disease," *Canadian Task Force on the Periodic Health Examination, Canadian Guide to Clinical Preventive Health Care, Ottawa: Health Canada*, 420-431, 1994.
Lutsoia et al., "Correlation of the Nitrate and Ascorbic Acid Content in Vegetables and Fruit," *Vopr. Pitan.*, 3:54-57, 1980 (Abstract).
Manola et al., "Prognostic Factors in Metastatic Melanoma: A Pooled Analysis of Eastern Cooperative Oncology Group Trials," *Journal of Clinical Oncology*, 18:3782-3793, 2000.
Margolis, "Therapy for Condyloma Acuminatum: A Review", *Reviews of Infections Diseases*, 4 supplement, S829-S836, 1982.
Maron, "Enamel erosion resulting from hydrochloric acid tablets," *JADA*, 127:781-784, 1996.
MayoClinic.com, "Periodontitis," Mayo Foundation for Medical Education and Research (*MFMER*), http://www.mayoclinic.com/health/periodontitis/DS00369/DSECTION=3, 2006.
McBride et al., "Role of Interbacterial Adherence in Colonization of the Oral Cavities of the Gnotobiotic Rats Infected with *Streptococcus mutans* and *Veillonella alcalescens*," *Immunity and Infection*, 33(2): 467-472, 1981.
Merck Manual Home Edition: Periodontitis.
National Cancer Institute: definition of Fruit Acid, obtained from the internet at http://www.cancer.gov/dictionary/?CdriD=613195 on Aug. 2, 2010.
Novotny et al., "Impact of ascorbic acid on selenium-induced growth inhibition of canine mammary tumor cells in vitro," *J. Nutr. Biochem.*, 4:341-345, 1993.
Office Communication issued in U.S. Appl. No. 10/497,504 dated Oct. 27, 2006.
Office Communication issued in U.S. Appl. No. 10/497,504 dated Jan. 3, 2007.
Office Communication issued in U.S. Appl. No. 10/497,504 dated Aug. 17, 2007.
Office Communication issued in U.S. Appl. No. 10/497,504 dated Jul. 16, 2008.
Office Communication issued in U.S. Appl. No. 10/497,504, dated Dec. 8, 2008.
Office Communication issued in U.S. Appl. No. 10/497,504, dated Jul. 31, 2009.
Perry, "Handbook of Inorganic Compounds," Taylor & Francis Group, Second Edition, 2011, pp. 548.
Rotruck, "Discovery of the Role of Selenium in Glutathione Peroxide," Selenium in Biology and Medicine, Eds. Spallholz, Martin, Ganther, AVI Publishing Co., pp. 10-16, 1981.
Socransky, "Relationship of Bacteria to the Etiology of Peridontal Disease," *Journal of Dental Research*, 49(2): 203-222, 1970.
Hussain et al., "Chemopreventive Action of Selenium on Methylcholanthrene-Induced Carcinogenesis in the Uterine Cervix of Mouse" *Oncology*, 49: 237-240, 1992.
Introduction to modern pharmaceuticals ($3^{rd}$ edition), Apr. 10, 1987, p. 414-416 (Japanese)—[Machine Translation provided].
Liang et al., "Sodium Selenite Induced HeLa Cells Apoptosis", *Nat Sci Ed*, 51(6): 663-667, 2005. (Chinese)—[English Abstract provided].

* cited by examiner

PHARMACEUTICAL PREPARATION CONTAINING SELENITE OR SELENITE-CONTAINING COMPOUNDS FOR TREATING CERVICAL DYSPLASIA OR CARCINOMAS

CROSS-REFERENCE TO RELATED APPLICATIONS

This application is a national phase application under 35 U.S.C. § 371 of International Application No. PCT/AT2012/000032 filed 16 Feb. 2012, which claims priority to Austrian Application No. A 201/2011 filed 16 Feb. 2011. The entire contents of each of the above-referenced disclosures is specifically incorporated herein by reference without disclaimer.

The present invention relates to pharmaceutical compositions containing selenite-containing compounds.

Inflammatory and/or degenerative alterations of the female cervix are a steadily increasing public health problem. Testing of cervical cell smears was developed by the Greek physician George Papanicolaou and the smears are classified according to the so-called Munich nomenclature II. Herein, the classification PAP I corresponds to a normal result, PAP II to a minor inflammatory and/or degenerative alteration, PAP III to cell profiles that cannot be assessed and need to be monitored, PAP IIID to a dysplasia, PAP IV to serious preliminary stages of carcinoma, and PAP V to a malign tumor. The forms of dysplasia PAP IIID and PAP IV are cytologically further differentiated into so-called "cervical intraepithelial neoplasias" (CIN) with the stages of CIN 1 for minor, CIN 2 for moderate, and CIN 3 for severe dysplasia. Analogously to the histological classification from CIN 1 (PAP IIID) to CIN 2 (also PAP IIID) to CIN 3 (PAP IV), it is also referred to the so-called Bethesda classification in the Anglo-American part of the world. Herein, the "Low-Grade Squamous Intraepithelial Lesion" (LSIL) corresponds to the Munich classification CIN 1, whereas cell alterations of a higher grade, i. e. "High-Grade Squamous Intraepithelial Lesions" (HSIL), correspond to the WHO classifications CIN 2 and CIN 3.

The average tendency for the regression of minor dysplasias (PAP IIID/CIN 1/LSIL) to a normal result (PAP I and PAP II, respectively) within a one-year period is as low as almost 15%. The tendency for the progression of minor dysplasias (PAP IIID/CIN 1/LSIL) to higher-grade dysplasias currently exhibits a mean annual transition probability of more than 7%, while the progression tendency of higher-grade dysplasias to carcinomas of the uterus is 0.74%.

Depending on the location and the severity of the cell alterations, the current international gynecological guidelines for the therapy of Cervical Intraepithelial Neoplasias (CIN) and microcarcinomas of the Cervix uteri comprise a destruction of the surface of the affected tissue, a conization with the aid of a scalpel, laser or LEEP (Loop Electrosurgical Excision Procedure) or a hysterectomy. Other non-surgical therapies are not known to date.

On the electrochemical level, inflammatory tissue processes are always associated with a (local) increase in so-called Reactive Oxygen Species (ROS), i. e. free radicals and peroxides. In the context of a spontaneous amelioration of these oxidative inflammatory factors, the competence of the body's own immune system and the levels of endogenous and exogenous antioxidants in the body play an important biological role. The anti-inflammatory and antiviral effects of antioxidative compositions have already been verified in numerous scientific publications and international patent documents (i. a. WO 2001/093910 A2 and WO 2003/047604 A1).

It was the object of the present invention to provide new means for the prevention and treatment of inflammations, dysplasias and/or carcinomas of the cervix.

Accordingly, the present invention relates to a pharmaceutical composition containing selenite-containing compounds and pharmaceutically acceptable acids, selected from citric acid, acetic acid, malic acid, carbonic acid, sulfuric acid, nitric acid, hydrochloric acid, fruit acids (e. g. malic acid, citric acid, tartaric acid, oxalic acid and fumaric acid, in particular citric acid) or mixtures thereof, for use in the treatment of inflammations, dysplasias and/or carcinomas of the cervix.

In the context of the present invention, it could surprisingly be found that a consequent local administration of antioxidative selenium-containing preparations (according to WO 2001/093910 A2 and WO 2003/047604 A1) in vivo also has a positive influence on negative cell alterations (dysplasias and carcinomas) within the scope of an early detection of cervical carcinoma. The present invention is suitable for both HPV-induced and non-HPV-induced disorders of the uterus. This is of great practical significance as the detection, or even specification, of the HPV is often omitted in gynecological practice because the positive detection of an HPV infection often has no influence on subsequent therapeutic decisions. However, the inventive treatment of non-HPV-induced uterine disorders (i. e. the use of the preparations according to the present invention in the treatment of or as a medication for inflammations, dysplasias and/or carcinomas of the cervix) is a particularly preferred embodiment of the present invention. Consequently, the present invention does not represent a strategy that is directed against a specific pathogen, but rather aims at a treatment of inflammations, dysplasias and/or carcinomas of the cervix in a directed manner, i. e. it may also be employed (long) after a potential pathogen has elicited the symptoms of a disease.

It has shown that a composition having an enhanced antioxidative potential may be provided by adding the above-mentioned acids to aqueous solutions of inorganic selenium compounds. Herein, the compositions prepared according to the present invention, i. e. in particular solutions, gels, emulsions, suspensions, ointments and the like, exhibit the therapeutic effects according to the present invention as—owing to the presence of the acids—they may be used in accordance with the present invention such as to, at least temporarily, maintain said enhanced antioxidative potential. This is the case if the enhanced antioxidative potential is still present at the time of administration at the therapy target destination and has not already been diluted, e. g. by administration solutions or body fluids, such as blood (e. g. in case of intravenous administration) or contents of the digestive tract (e. g. in case of oral application).

Accordingly, the present invention preferably relates to the topical, mucosal and intravaginal administration of these preparations for external use (i. e. topical or buccal) or for the direct administration to mucous membranes (mucosal application). Typical formulations for administration that are suitable for a topical, mucosal or intravaginal administration are known to a person skilled in the art and have been described in the relevant pharmacopoeias.

In addition to the essential ingredients of selenite and the above-mentioned acids, the composition according to the present invention may also contain further suitable ingredients and/or pharmaceutically acceptable excipients. The composition according to the present invention preferably contains selenite in an amount between 1 and 500 mg, more preferably between 10 and 100 mg, in particular between 30 and 70 mg, per 100 g of the composition. Preferably, the composition according to the present invention contains selenite in the form of sodium selenite (which is mostly present as a pentahydrate compound which starts to release crystal water at 40° C.)

Independently, the composition according to the present invention preferably contains one or more acids in a total amount between 1 mg and 10 g acid, more preferably between 10 mg and 5 g acid, in particular between 100 mg and 1 g acid, per 100 g of the composition (in particular if the acid is added in its solid form). Alternatively, the acid may also be added in its liquid form (e. g. with water, i. e. as an aqueous solution). Water and aqueous solutions, respectively, optionally containing further ingredients, may be added to the composition according to the present invention in an amount between 0 and (about) 99.9 g, preferably between 50 and 99 g, in particular between 80 and 98 g, per 100 g of the composition.

According to a preferred embodiment, the present invention is provided in the form of a gel. Accordingly, the composition according to the present invention preferably contains a gelling agent. Both inorganic and organic aqueous gelling agents may be used as a gelling agent. Particularly suitable gelling agents are cellulose derivatives, in particular carboxymethylcellulose, methylcellulose, hydroxypropylcellulose and, in particular, hydroxyethylcellulose. Preferably, the gelling agents, in particular hydroxyethylcellulose, are used at a total concentration of between 0.1 g and 30 g, more preferably between 0.5 g and 5 g, in particular between 1 g and 3 g, per 100 g of the composition.

A particularly preferred embodiment of the gel composition according to the present invention contains silicon dioxide, in particular highly dispersed silicon dioxide, e. g. according to WO 2001/85852 A1, as a technological suspension medium and/or as an adsorbent. Preferably, an amount between 100 mg and 50 g, more preferably between 500 mg and 10 g, in particular between 1 g and 5 g, $SiO_2$ per 100 g of the composition is used.

The composition according to the present invention preferably has a pH-value of less than 7.0, more preferably less than 5.0, in particular between 4.0 and 2.5.

The composition according to the present invention is preferably present in the form of a solution, emulsion, ointment or sponge (tampon). Advantageously, the composition may contain further excipients and/or further active ingredients, in particular buffer substances, coloring agents, stabilizers, preservatives, carrier substances or combinations thereof. Preferred examples of such substances are maltodextrin, flavoring agents, such as e. g. lemon flavor, peppermint oil, potassium sorbate and sodium benzoate (as preservatives), and the like.

Preferred further active ingredients are antibiotics, antiviral agents, antimycotics, pain inhibitors, anti-inflammatory agents or combinations thereof.

The composition according to the present invention has surprisingly proved to be particularly effective in the treatment of cervical cell alterations having a PAP score of ≥PAP III and/or a CIN score of ≥CIN 1. In particular, the present invention may be used in the treatment of cervical inflammations having a PAP score of PAP III and PAP IIID.

Furthermore, it is to be pointed out that the present invention is suitable for the treatment of cervical carcinomas.

According to a further aspect, the present invention relates to a method for the treatment of inflammations, dysplasias and/or carcinomas of the cervix, in which the compositions according to the present invention are administered in an effective amount to patients suffering from the above disorders. Preferred dosages may range (e. g. when present as a gel) between 0.005 g and 0.1 g of sodium selenite pentahydrate per 100 g of the gel, in particular between 0.01 g and 0.1 g per 100 g of the gel.

The present invention will be explained in more detail by way of the following Examples, without being limited thereto.

EXAMPLE 1

Preparation of an Acidified Sodium Selenite Gel

An acidified sodium selenite gel was prepared in the following composition (per 100 g):

| | |
|---|---|
| Sodium selenite pentahydrate | 0.050 g |
| Silicon dioxide, highly dispersed | 0.200 g |
| Citric acid | 0.496 g |
| Sodium benzoate | 0.050 g |
| Potassium sorbate | 0.099 g |
| Hydroxyethylcellulose | 1.985 g |
| Water | 97.120 g |
| | 100.000 g |

EXAMPLE 2

Treatment of Cervical Dysplasias

Design: Multicenter pilot study
Inclusion criteria: Age >19 years
PAP≥III<IV
Implementation:
Intravaginal administration of 5 ml of sodium selenite gel 1×per day in case of a diagnosis of PAP≥III<IV over a period of 90 days. The administration is to be discontinued during menstruation. Follow-up examination after 90 days of gel administration.
Results:
Of 31 patients 27 (87.1%) exhibited a response; 4 patients (12.9%) were non-responders.

EXAMPLE 3

Effects of the Acidified Sodium Selenite Gel

| Initials | Age | First ward round | last ward round | PAP start | PAP end | HPV start | HPV end |
|---|---|---|---|---|---|---|---|
| CC | 45 | 15 Jul. 2010 | 05 Oct. 2010 | III D | II | neg. | n.d. |
| AU | 47 | 20 Jul. 2010 | 12 Oct. 2010 | III D | II | n.d. | n.d |
| IG | 28 | 20 Jul. 2010 | 09 Sep. 2010 | IV | IV | pos. | n.d. |
| NK | 34 | 03 Aug. 2010 | 03 Nov. 2010 | III D | III | neg. | n.d. |
| KS | 44 | 03 Aug. 2010 | 03 Nov. 2010 | III | III | neg. | n.d. |
| RS | 19 | 21 Jul. 2010 | 28 Oct. 2010 | III D | III D | pos. | pos. |
| BK | 49 | 27 Jul. 2010 | 27 Oct. 2010 | III D | II | pos. | n.d. |
| MJ | 42 | 27 Jul. 2010 | 27 Oct. 2010 | III D | II | n.d. | n.d. |
| AU | 19 | 14 Apr. 2010 | 03 Nov. 2010 | III D | II | pos. | n.d. |
| TF | 25 | 28 Jul. 2010 | 28 Oct. 2010 | III D | II | pos. | neg. |
| RH | 49 | 28 Jul. 2010 | 28 Oct. 2010 | III D | II | n.d. | n.d. |
| SH | 32 | 29 Jul. 2010 | 02 Nov. 2010 | III D | II | pos. | n.d. |

-continued

| Initials | Age | First ward round | last ward round | PAP start | PAP end | HPV start | HPV end |
|---|---|---|---|---|---|---|---|
| AK | 27 | 02 Aug. 2010 | 03 Nov. 2010 | III D | II | pos. | n.d. |
| SL | 27 | 29 Jul. 2010 | 29 Oct. 2010 | III | II | pos. | n.d. |
| AG | 71 | 02 Aug. 2010 | 04 Nov. 2010 | III | II | n.d. | pos. |
| ER | 28 | 26 Aug. 2010 | 02 Nov. 2010 | III D | II | pos. | pos. |
| BS | 53 | 10 May 2010 | 30 Sep. 2010 | III D | III D | pos. | n.d. |
| RS | 52 | 23 Jun. 2010 | 11 Nov. 2010 | III | III | neg. | neg. |
| DG | 48 | 18 May 2010 | 02 Nov. 2010 | III D | II | n.d. | n.d. |
| MJ | 19 | 10 May 2010 | 09 Aug. 2010 | III D | II | pos. | neg. |
| RM | 62 | 27 May 2010 | 06 Oct. 2010 | III | II | n.d. | n.d. |
| AF | 38 | 22 Jun. 2010 | 16 Aug. 2010 | III D | II | pos. | n.a. |
| MF | 49 | 28 Jul. 2010 | 30 Jun. 2010 | III D | II | pos. | pos. |
| PK | 56 | 26 May 2010 | 02 Nov. 2010 | III D | II | neg. | n.d. |
| IR | 41 | 08 Jun. 2010 | 17 Aug. 2010 | III | IV | n.d. | n.d. |
| BP | 56 | 14 Jun. 2010 | 03 Nov. 2010 | III D | II | pos. | n.a. |
| EN | 47 | 02 Jun. 2010 | 11 Nov. 2010 | III D | II | pos. | n.a. |
| IP | 40 | 26 Jul. 2010 | 26 Aug. 2010 | III D | II | pos. | n.a. |
| MW | 47 | 26 Jul. 2010 | 26 Aug. 2010 | III D | n.d. | n.d. | n.a. |
| MR | 50 | 02 Aug. 2010 | 02 Sep. 2010 | III D | IV | pos. | n.a. |
| DB | 22 | 08 Jul. 2010 | 11 Nov. 2010 | II | II | pos. | n.a. |
| YT | 32 | 19 Aug. 2010 | 11 Nov. 2010 | III | II | n.d. | n.a. |
| KP | 67 | 10 Aug. 2010 | 03 Nov. 2010 | III | II | neg. | n.d. |
| RK | 45 | 24 Jun. 2010 | 20 Sep. 2010 | III | II | neg. | neg. |
| CS | 50 | 30 Aug. 2010 | 08 Nov. 2010 | III | III | n.d. | n.a. |
| ML | 28 | 03 Aug. 2010 | 03 Nov. 2010 | III | II | neg. | |
| FP | 43 | 10 Aug. 2010 | 11 Nov. 2010 | III D | II | pos. | n.d. |
| CD | 44 | 07 Sep. 2010 | 14 Dec. 2010 | III D | II | pos. | n.d. |
| KW | 21 | 12 Aug. 2010 | 30 Nov. 2010 | III D | III D | pos. | n.d. |
| EL | 52 | 13 Aug. 2010 | 18 Nov. 2010 | III | II | n.d. | n.d. |
| ES | 38 | 10 Aug. 2010 | 21 Sep. 2010 | III | II | n.d. | n.d. |
| GT | 56 | 14 Sep. 2010 | 14 Dec. 2010 | III D | II | n.d. | n.d. |
| BM | 40 | 20 Aug. 2010 | 10 Nov. 2010 | III D | II | n.d. | n.d. |
| MP | 47 | 30 Jul. 2010 | 16 Nov. 2010 | III D | III | D pos. | pos. |
| GS | 38 | 19 Aug. 2010 | 14 Dec. 2010 | III D | II | n.d. | n.d. | n.d.: not determined
n.a.: not available
neg.: negative
pos.: positive

By the application of the acidified sodium selenite gel in two patients it could be shown that the gel exhibits an effect according to the present invention and may be used in the treatment of cervical dysplasia in an efficient manner.

EXAMPLE 4

Treatment of a Squamous Cell Carcinoma of the Cervix uteri in a 38-year-old Patient with Acidified Sodium Selenite Gel (Prepared According to Example 1)

Due to a pronounced dysplasia of the uterus (stage PAP IV, bioptic according to CIN 3) patient IG, born on 31 Dec. 1975, was subjected to a conization and a curettage of the cervix during her hospitalization period from 29 May 2008 to 2 Jun. 2008 at a general public hospital in Austria. Further examinations, including the histological examination of a tissue sample obtained from the patient, resulted in the diagnosis of an invasive squamous cell carcinoma of the Cervix uteri and of a carcinoma in situ with stage FIGU IB 1. This result was confirmed in a subsequent in-patient stay at the gynecological department of another Austrian hospital.

CT, MRI and sonographic examinations resulted in the diagnosis of an obviously malign tumor with a size of 10 to 12 mm located in the cranial region of the Cervix uteri, already spreading to the Isthmus uteri, but yet without lymphogenic metastatic spread. Not least because of the location of the residual tumor in the region of the Isthmus uteri, these results led to a therapeutic recommendation for radical surgery according to Wertheim PIVER II as any uterus-preserving surgery was not possible given the location of the tumor. Despite the enormous time pressure for making a decision, the patient obtained a second medical opinion and finally decided to undergo a potentially uterus-preserving therapy with the preparation according to the present invention. After a four-month period of therapy with the gel according to the present invention, a continuous gynecological, radiological and histological monitoring of the patient yielded a substantial reduction in tumor size as well as a remission of the inflammation. After two further months of therapy with the preparation according to the present invention the tumor had vanished and the histological smear yielded a remission of the inflammation to PAP II+.

The invention claimed is:

1. A method comprising: obtaining a pharmaceutical composition comprising at least one selenite-containing compound, a highly dispersed silicon dioxide, and at least one pharmaceutically acceptable acid selected from the group comprising citric acid, acetic acid, malic acid, carbonic acid, sulfuric acid, nitric acid, hydrochloric acid, or a fruit acid wherein the composition is further defined as a gel; and administering the composition intravaginally to a subject having cervical cell alterations with a PAP score of ≥PAP III and/or a CIN score of ≥CIN 1; wherein the cervical cell alterations with the PAP score of ≥PAP III and/or a CIN score of ≥CIN 1 are treated in the subject; wherein the cervical cell alterations are not a malignant tumor; wherein the cervical cell alterations are not human papillomavirus (HPV)-induced; and wherein administration is discontinued during menstruation of the subject.

2. The method of claim 1, wherein the composition comprises a gelling agent.

3. The method of claim 1, wherein the composition comprises an aqueous gelling agent.

4. The method of claim 3, wherein the aqueous gelling agent is a cellulose derivative.

5. The method of claim 4, wherein the gelling agent is further defined as carboxymethylcellulose, hydroxypropylcellulose, methylcellulose and hydroxyethylcellulose.

6. The method of claim 1, wherein the composition has a pH of less than 7.0.

7. The method of claim 6, wherein the composition has a pH of less than 5.0.

8. The method of claim 7, wherein the composition has a pH between 4.0 and 2.5.

9. The method of claim 1, wherein the composition further comprises at least one buffer substance, coloring agent, stabilizer, and/or carrier substance.

10. The method of claim 1, further comprising at least one antibiotic, antiviral agent, antimycotic, pain inhibitor, and/or anti-inflammatory agent.

11. The method of claim 1, wherein the subject has cervical cell alterations having a PAP score of PAP III, PAP IIID, or both.

12. The method of claim 1, where in the acid is further defined as citric acid.

13. The method of claim 1, wherein the ate least one selenite-containing composition is sodium selenite pentahydrate.

14. A method comprising: obtaining a pharmaceutical composition comprising: sodium selenite pentahydrate; citric acid; dispersed silicon dioxide; and a gelling agent; and administering the composition intravaginally to a subject having cervical cell alterations with a PAP score of ≥PAP III and/or a CIN score of ≥CIN 1; wherein the cervical cell alterations with the PAP score of ≥PAP III and/or a CIN score of ≥CIN 1 are treated in the subject; wherein the cervical cell alterations are not a malignant tumor; wherein the cervical cell alterations are not human papillomavirus (HPV)-induced; and wherein administration is discontinued during menstruation of the subject.

15. The method of claim 14, wherein the aqueous gelling agent is a cellulose derivative.

16. The method of claim 15, wherein the aqueous gelling agent is hydroxyethylcellulose.

17. The method of claim 14, wherein the composition has a pH between 4.0 and 2.5.

18. The method of claim 14, wherein the subject has cervical cell alterations resulting in a PAP score of PAP III, PAP IIID, or both.

19. A method comprising: obtaining a pharmaceutical composition, the composition comprising at least one selenite-containing compound, a highly dispersed silicon dioxide, and at least one pharmaceutically acceptable acid selected from the group comprising citric acid, acetic acid, malic acid, carbonic acid, sulfuric acid, nitric acid, hydrochloric acid, or a fruit acid wherein the composition is further defined as a gel; and administering the composition intravaginally to a subject having cervical cell alterations with a PAP score of ≥PAP III and/or a CIN score of ≥CIN 1; wherein the cervical cell alterations with the PAP score of ≥PAP III and/or a CIN score of ≥CIN 1 are treated in the subject; wherein the cervical cell alterations are not a malignant tumor; wherein the cervical cell alterations are not human papillomavirus (HPV)-induced; and wherein said administering to the subject is performed once daily and wherein administration is discontinued during menstruation of the subject.

20. The method of claim 19, wherein said administering is performed until a remission of the cervical cell alterations has occurred.

21. The method of claim 1, wherein said administering is performed until a remission of the cervical cell alterations has occurred.

* * * * *